United States Patent
Learmonth

(10) Patent No.: US 9,845,316 B2
(45) Date of Patent: *Dec. 19, 2017

(54) CRYSTAL FORMS OF 5-[3-(2,5-DICHLORO-4, 6-DIMETHYL-1-OXY-PYRIDINE-3-YL)[1,2,4] OXADIAZOL-5-YL]-3-NITROBENZENE-1,2-DIOL

(71) Applicant: BIAL—PORTELA & CA., S.A. ("PORTELA"), S. Mamede do Coronado (PT)

(72) Inventor: David Alexander Learmonth, Alfena (PT)

(73) Assignee: BIAL—PORTELA & CA., S.A., S. Mamede do Coronado (PT)

(*) Notice: Subject to any disclaimer, the term of this patent is extended or adjusted under 35 U.S.C. 154(b) by 0 days.

This patent is subject to a terminal disclaimer.

(21) Appl. No.: 14/628,630

(22) Filed: Feb. 23, 2015

(65) Prior Publication Data

US 2015/0166519 A1 Jun. 18, 2015

Related U.S. Application Data

(63) Continuation of application No. 12/933,044, filed as application No. PCT/PT2009/000013 on Mar. 16, 2009, now Pat. No. 8,975,410.

(60) Provisional application No. 61/069,721, filed on Mar. 17, 2008.

(51) Int. Cl.
*A61K 31/4439* (2006.01)
*C07D 413/04* (2006.01)

(52) U.S. Cl.
CPC ........ *C07D 413/04* (2013.01); *C07B 2200/13* (2013.01)

(58) Field of Classification Search
CPC .................................................. A61K 31/4439
USPC ....................................................... 514/340
See application file for complete search history.

(56) References Cited

U.S. PATENT DOCUMENTS

| | | | |
|---|---|---|---|
| 1,532,178 A | 4/1925 | Godbold | |
| 3,647,809 A | 3/1972 | Reiter et al. | |
| 4,065,563 A | 12/1977 | Narayanan et al. | |
| 4,264,573 A | 4/1981 | Powell et al. | |
| 4,386,668 A | 6/1983 | Parish | |
| 4,963,590 A | 10/1990 | Backstrom et al. | |
| 5,236,952 A | 8/1993 | Bernauer et al. | |
| 5,476,875 A | 12/1995 | Bernauer et al. | |
| 5,633,371 A | 5/1997 | Bernauer et al. | |
| 5,705,703 A | 1/1998 | Bernauer et al. | |
| 5,840,769 A | 11/1998 | Kolter et al. | |
| 6,206,110 B1 | 3/2001 | Slaughter, Jr. et al. | |
| 6,500,867 B1 | 12/2002 | Virkki et al. | |
| 6,509,363 B2 | 1/2003 | Salituro et al. | |
| 6,512,136 B1 | 1/2003 | Benes et al. | |
| 6,521,136 B1 | 2/2003 | Sfez et al. | |
| 6,627,646 B2 | 9/2003 | Bakale et al. | |
| 6,660,753 B2 | 12/2003 | Van Wagenen et al. | |
| 7,041,685 B2 | 5/2006 | Cai et al. | |
| 7,112,595 B2 | 9/2006 | Wagenen et al. | |
| 7,144,876 B2 | 12/2006 | Cai et al. | |
| 7,317,029 B2 | 1/2008 | Cai et al. | |
| 7,435,750 B2 | 10/2008 | Cai et al. | |
| 7,553,964 B2 | 6/2009 | Liu et al. | |
| 8,168,793 B2 | 5/2012 | Learmonth et al. | |
| 8,524,746 B2 | 9/2013 | Learmonth et al. | |
| 8,536,203 B2 | 9/2013 | Learmonth et al. | |
| 8,975,410 B2* | 3/2015 | Learmonth .......... | C07D 413/04 546/269.4 |
| 2002/0012701 A1 | 1/2002 | Kolter et al. | |
| 2003/0055085 A1 | 3/2003 | Wagenen et al. | |
| 2004/0097555 A1 | 5/2004 | Ohkawa et al. | |
| 2004/0138281 A1 | 7/2004 | Wikstrom et al. | |
| 2004/0171645 A1 | 9/2004 | Bartoszyk et al. | |
| 2006/0019956 A1 | 1/2006 | Green | |
| 2006/0160812 A1 | 7/2006 | Schubert et al. | |
| 2006/0173074 A1 | 8/2006 | Ellmen et al. | |
| 2006/0257473 A1 | 11/2006 | Puranajoti | |
| 2007/0048384 A1 | 3/2007 | Rosenberg et al. | |
| 2007/0078133 A1 | 4/2007 | Liu et al. | |
| 2007/0219187 A1 | 9/2007 | Bessis et al. | |
| 2007/0299110 A1 | 12/2007 | Gagliardi et al. | |
| 2008/0051441 A1 | 2/2008 | Brown et al. | |
| 2008/0071184 A1 | 3/2008 | Carter | |
| 2008/0167286 A1 | 7/2008 | Gopalakrishnan et al. | |
| 2008/0269236 A1 | 10/2008 | Ji et al. | |
| 2009/0000437 A1 | 1/2009 | Johnson et al. | |
| 2009/0054437 A1 | 2/2009 | Learmonth et al. | |
| 2009/0111778 A1 | 4/2009 | Apodaca et al. | |

(Continued)

FOREIGN PATENT DOCUMENTS

| | | |
|---|---|---|
| CN | 1173926 | 5/2001 |
| CN | 1340500 | 3/2002 |
| DE | 3740383 A1 | 6/1988 |
| EP | 0237929 B1 | 9/1987 |
| EP | 0372654 | 6/1990 |
| EP | 0487774 | 11/1990 |
| EP | 0462639 | 12/1997 |
| EP | 1167342 A1 | 1/2002 |
| EP | 1845097 A1 | 10/2007 |
| EP | 1881979 A1 | 1/2008 |
| FR | 1260080 | 5/1961 |
| JP | 10-67651 A | 3/1998 |
| JP | 2002-20319 A | 1/2002 |
| JP | 2003-116966 A | 4/2003 |

(Continued)

OTHER PUBLICATIONS

Kalinderi et al., "Pharmacological treatment, etc.," Int J Clin Pract., 2011, 65, 12, 1289-1294.*

(Continued)

*Primary Examiner* — Patricia L Morris
(74) *Attorney, Agent, or Firm* — The Marbury Law Group, PLLC

(57) ABSTRACT

This invention relates to novel polymorphs of $(HO)_2NO_2(C_6H)$—$(C_2N_2O)$—$(C_5N)(CH_3)_2Cl_2O$, to processes for their preparation, and to pharmaceutical compositions containing said novel polymorphs as active pharmaceutical ingredient.

5 Claims, No Drawings

(56) References Cited

U.S. PATENT DOCUMENTS

| | | |
|---|---|---|
| 2009/0162283 A1 | 6/2009 | Bando et al. |
| 2009/0227626 A1 | 9/2009 | Deraeve et al. |
| 2009/0312347 A1 | 12/2009 | Dahl et al. |
| 2010/0004284 A1 | 1/2010 | Farina et al. |
| 2010/0112301 A1 | 5/2010 | Powers |
| 2010/0113529 A1 | 5/2010 | Learmonth et al. |
| 2010/0168113 A1 | 7/2010 | Learmonth et al. |
| 2010/0256193 A1 | 10/2010 | Cardoso De Vasconcelos et al. |
| 2010/0256194 A1 | 10/2010 | Cardoso De Vasconcelos et al. |
| 2011/0014282 A1 | 1/2011 | De Vasconcelos |
| 2011/0112301 A1 | 5/2011 | Learmonth et al. |
| 2011/0301204 A1 | 12/2011 | De Almeida et al. |
| 2012/0196904 A1 | 8/2012 | Learmonth et al. |
| 2013/0324578 A1 | 12/2013 | Soares Da Silva et al. |
| 2013/0331416 A1 | 12/2013 | Learmonth et al. |
| 2014/0024682 A1 | 1/2014 | Learmonth et al. |
| 2014/0045900 A1 | 2/2014 | Soares Da Silva et al. |
| 2014/0350057 A1 | 11/2014 | Russo et al. |
| 2015/0072977 A1 | 3/2015 | Learmonth et al. |
| 2015/0166519 A1 | 6/2015 | Learmonth |

FOREIGN PATENT DOCUMENTS

| | | |
|---|---|---|
| JP | 2008-162955 A | 7/2008 |
| WO | 93/13083 A1 | 7/1993 |
| WO | 00/37423 | 6/2000 |
| WO | 01/12627 A1 | 2/2001 |
| WO | 01/68083 A1 | 9/2001 |
| WO | 02/17175 A1 | 2/2002 |
| WO | 02/68417 A2 | 6/2002 |
| WO | 02/051442 A1 | 7/2002 |
| WO | 02/096867 A2 | 12/2002 |
| WO | 02/100826 A2 | 12/2002 |
| WO | 2005/013982 A1 | 2/2005 |
| WO | 2005/044797 A1 | 5/2005 |
| WO | 2005/105780 A3 | 11/2005 |
| WO | 2006/061697 A1 | 6/2006 |
| WO | 2006/071184 A1 | 7/2006 |
| WO | 2006/114400 A1 | 11/2006 |
| WO | 2006/129199 A1 | 12/2006 |
| WO | 2006/132914 A1 | 12/2006 |
| WO | 2007/013830 A1 | 2/2007 |
| WO | 2007/113276 A1 | 10/2007 |
| WO | 2007/117165 A1 | 10/2007 |
| WO | 2008/021388 A1 | 2/2008 |
| WO | 2008/094053 A1 | 8/2008 |
| WO | 2008/118331 A2 | 10/2008 |
| WO | 2009/029632 A1 | 3/2009 |
| WO | 2009/116882 A1 | 9/2009 |
| WO | 2010/014025 A1 | 2/2010 |
| WO | 2011/107653 A1 | 9/2011 |
| WO | 2012/107708 A1 | 8/2012 |
| WO | 2013/089573 A1 | 6/2013 |

OTHER PUBLICATIONS

Ma et al., "Structure-based, etc.," Br J Clin Pharmacol 77:3, 2013, 410-420.*
Almeida et al., "The Evolution, etc.," Recent Patents on CNS Drug Discovery, 2008, 3, 50-54.*
Espinoza et al., "Role of Catechol, etc.," CNS & Neurological Disorders—Drug Targets, 2012, 11, 251-263.*
Co-pending U.S. Appl. No. 12/226,260, filed May 28, 2009, to Learmonth et al., titled: New Pharmaceutical Compounds.
Co-pending U.S. Appl. No. 12/524,848, filed Dec. 30, 2009, to Learmonth et al., titled: Dosage Regimen for COMT Inhibitors.
Co-pending U.S. Appl. No. 12/933,044, filed Sep. 16, 2010, to Learmonth et al.: Titled: Crystal Forms of 5-[3-(2,5-Dichloro-4,6-Dimethyl-1-Oxy-Pyridine-3-yl)[1,2,4] Oxadiazol-5-yl]-3-Nitrobenzene-1,2-Diol.
Co-pending U.S. Appl. No. 13/002,287, filed Jul. 29, 2009, to Almeida et al., Titled: Administration Regime for Nitrocatechols.
Co-pending U.S. Appl. No. 13/442,356, filed Apr. 9, 2012, to Learmonth et al., Titled: Nitrocatechol Derivatives as COMT Inyhibitors.
Co-pending U.S. Appl. No. 13/583,375, filed Oct. 21, 2011, to Soares de Silva et al., Titled: Administration Regime for Nitrocatechols.
Database Caplus [Online], Chemical Abstracts Service, Columbus, Ohio, US XP002440393, retrieved from STN accession No. 2003:365244, Database accession No. 138:337989, Abstract.
EPO Search Report and Written Opinion for EPO Patent Application No. 06075343, dated Mar. 28, 2006.
Girges et al., "Synthesis of Nicotinoyl Hydrazones, Their N-Oxide Analogs and the Corresponding 3-(5-Aryl-1,3,4-oxadiazol-2-yl)pyridine Derivatives as Potential Hypoglycemic Agents," Chemical Papers (1992), 46(4), 272-277.
Howse, "Brocesine in Parkinson's disease, Action of a peripheral and central decarboxylase inhibitor in potentiating levodopa," Journal of Neurology, Neurosurgery, and Psychiatry, 36, pp. 27-29 (1973).
International Preliminary Report on Patentability for Int'l Patent Application No. PCT/PT2007/000016, dated Oct. 14, 2008.
International Search Report and Written Opinion for Int'l Patent Application No. PCT/PT2007/000016, dated Jul. 13, 2007.
International Search Report and Written Opinion in PCT/PT2008/000042, dated Apr. 29, 2009.
Advisory Action issued in co-pending U.S. Appl. No. 12/750,956, dated Dec. 2, 2013.
International Search Report for Patent Application No. PCT/PT2007/000043, dated Apr. 23, 2008.
International Search Report and Written Opinion for PCT/PT2009/000044, dated Nov. 16, 2009.
International Preliminary Report on Patentability for PCT/PT2009/000044, dated Feb. 10, 2011.
Office Action issued in co-pending U.S. Appl. No. 12/750,956, dated Dec. 22, 2014.
Korolkovas, A., "Essentials of Medicinal Chemistry," Development of Drugs, Second Ed., pp. 97-103 and 135-137 (1998).
Krogsgaard-Larsen, P., et al., Textbook of Drug Design and Discovery, Third Ed., Table 14.3, pp. 426-427 (2002).
Learmonth, David A., et al., "Chemical Synthesis and Characterization of Conjugates of a Novel Catechol-O-methyltransferase Inhibitor," Bioconjugate Chem., vol. 13, pp. 1112-1118, American Chemical Society (2002).
Morbus Parkinson, Stellenwert von COMT-Hemmern Bestatigt, May 3, 2004, 2 pages.
Nutt, John G., et al., "Pharmacokinetics of Levodopa," Clinical Neuropharmacology, vol. 7, No. 1, pp. 35-49, Raven Press, (1984).
Nutt, John G., "Catechol-O-methyltransferase Inhibitors for treatment of Parkinson's disease," Commentary, vol. 351, pp. 1221-1222, The Lancet (Apr. 1998).
Office Action issued in co-pending U.S. Appl. No. 12/226,260, dated Mar. 20, 2012.
Office Action issued in co-pending U.S. Appl. No. 12/226,260, dated Nov. 5, 2012.
Office Action in co-pending U.S. Appl. No. 12/524,848, dated Apr. 26, 2012.
Office Action in co-pending U.S. Appl. No. 12/524,848, dated Oct. 29, 2012.
Office Action in co-pending U.S. Appl. No. 12/524,848, dated Jan. 18, 2013.
Office Action in co-pending U.S. Appl. No. 12/750,957, dated Jan. 7, 2013.
Parashos, Sotirios A., et al., "Frequency, Reasons, and Risk Factors of Entacopone Discontinuation in Parkinson Disease," Clin Neuropharmacol, vol. 27, No. 3, pp. 119-123 (Jun. 2004).
Pedrosa, R., et al., "Oxidatve and non-oxidative mechanisms of neuronal cell death and apoptosis by L-3,4-dihydroxyphenylalanine (L-DOPA) and dopamine," British Journal of Pharmacology, vol. 137, pp. 1305-1313 (2002).
Poulain, R.F. et al., "Parallel Synthesis of 1,2,4-oxadiazoles from carboxylic acids using an improved uranium-based, activation," Tetrahedron Letters, 42:1495-1498 (2001).

(56) References Cited

OTHER PUBLICATIONS

Reches, A., et al., "3-O-Methyldopa inhibits rotations induced by levodopa in rats after unilateral destruction of the nigrostriatal pathway," Official Journal of the American Academy of Neurology, vol. 32, No. 8, pp. 887-888, Neurology, (Aug. 1982).

Smith, Kirsten S., et al., "In vitro Metabolism of Tolcapone to Reactive Intermediates: Relevance to Tolcapone Liver Toxicity," Chem. Res. Toxicol., vol. 16, pp. 123-128, American Chemical Society, (2003).

Soares de Silva, P., et al., "The O-methylated derivative of L-DOPA, 3-O-methyl-L-DOPA, fails to inhibit neuronal and non-neuronal aromatic L-amino acid decarboxylase," Brain Research, vol. 863, pp. 293-297 (2000).

Tervo, Anu J., et al., "A structure-activity relationship study of catechol-O-methyltransferase Inhibitors combining molecular docking and 3D QSAR methods," Journal of Computer-Aided Molecular Design, vol. 17, pp. 797-810 (2003).

Tohgi, H. et al., "The significance of 3-O-metyldopa concentration in the cerebrospinal fluid in the pathogenesis of wearing-off phenomenon in Parkinson's disease," Neuroscience Letters, vol. 132, pp. 19-22, (1991).

Vieira-Coelho, M.A., et al., "Effect of tolcapone upon soluble and membrane-bound brain and liver catechol-O-methyltransferase," Brain Research, vol. 821, pp. 69-78 (1999).

Ansel et al., (Ansel's Pharmaceutical Dosage Forms and Drug Delivery systems. 6th edition 1995).

Kristensen et al. "Granulation: A Review on Pharmaceutical Wet-Granulation," Drug Development and Industrial Pharmacy, 13(4 &5), 803-872 (1987).

Co-pending application PCT/PT2010/000014, filed Mar. 31, 2010 to Bial-Portela & CA, S.A.; Titled: Pharmaceutical Formulation Comprising Nitrocatechol Derivatives and Methods of Making Thereof.

Co-pending application PCT/PT2010/000015, filed Mar. 31, 2010 to Bial-Portela & CA, S.A.: Titled: Pharmaceutical Formulation Comprising Nitrocatechol Derivatives and Methods of Making the Same.

Co-pending U.S. Appl. No. 12/750,957, filed Mar. 31, 2010 to Teofilo Cardoso de Vasconcelos et al.; Titled: Pharmaceutical Formulation Comprising Nitrocatechol Derivatives and Methods of making the Same.

International Search Report in co-pending application PCT/PT2010/000014 dated Jun. 22, 2010.

Written Opinion of the International Searching Authority in co-pending application PCT/PT2010/000014 dated Jun. 22, 2010.

Al-Mousawi, S.M. et al., "Alkylazinylcarbonitriles as building blocks in heterocyclic synthesis: a route for the synthesis of 4-methyl-2-oxopyridines," Pharmazie, 54, 8, pp. 571-574 (1999).

Al-Omran, F. et al., "Heterocyclic Synthesis via Enaminones: Novel Synthesis of (1H)-Pyridin-2-one, Pyrazolo [1-5-α] pyrimidine and Isoxazole Derivatives Incorporating a N-Methylphthalimide and Their Biological Evaluation," J. Heterocyclic Chem., 42, pp. 307-312 (2005).

Bondvalli et al., "An Efficient Synthesis of Functionalized 2-Pyridones by Direct Route or via Amide/Enolate Ammoniu Salt Intermediates," Synthesis, No. 7, pp. 1169-1174 (1999).

Davies, Ian W. et al., "A General [3+2+1] Annulation Strategy for the Preparation of Pyridine N-Oxides," Organic Letters, vol. 3, No. 2, pp. 209-211 (2001).

Marcoux, Jean-Francois et al., A General Preparation of Pyridines and Pyridones via the Annulation of Ketones and Esters, J. Org. Chem, 66, pp. 4194-4199 (2001).

English language translation of JP 2003-116966 dated Apr. 22, 2003.

Non-Final Office Action issued in co-pending U.S. Appl. No. 12/750,957, dated Oct. 10, 2013.

Final Office Action issued in co-pending U.S. Appl. No. 12/750,957, dated Jun. 12, 2014.

Australian Office Action for co-pending AU Patent Application No. 2010231961, dated Apr. 14, 2014.

Australian Office Action for co-pending AU Patent Application No. 2010231962, dated Apr. 14, 2014.

Japanese Office Action for co-pending JP Application No. 2012-503350, dated Apr. 23, 2014 with English language translation.

Japanese Office Action for co-pending JP application No. 2012-503351, dated Apr. 23, 2014, with English language translation.

Russian Office Action for co-pending RU Application No. 2011144145, dated Apr. 22, 2014, with English language translation.

Chinese First Office Action for co-pending CN Application No. 201080022653.X, dated Dec. 3, 2012, with English language translation.

Chinese Second Office Action for co-pending CN Application No. 201080022653.X, dated Jan. 23, 2014, with English language translation.

International Preliminary Report on Patentability and Written Opinion for PCT/PT2010/00014, dated Oct. 13, 2011.

International Search Report and Written Opinion for PCT/PT2010/000015, dated Nov. 23, 2010.

Ivanova, LA, "Technology of Medicinal Forms," Moscow, "Medicina", vol. 2, 1991, pp. 223-224, English translation.

Chinese Third Office Action for co-pending CN Application No. 201080022653.X, dated Jan. 22, 2015 with English language translation.

Co-pending U.S. Appl. No. 12/750,956, filed Mar. 31, 2010 to Teofilo Cardoso de Vasconcelos et al., Titled: Pharmaceutical Formulation Comprising Nitrocatechol Derivatives and Methods of Making Thereof.

Office Action issued in co-pending U.S. Appl. No. 12/750,956, dated Oct. 15, 2012.

Mexican Office Action for co-pending MX Application No. 2011-010415, dated Aug. 19, 2014, with English language translation.

Office Action issued in co-pending U.S. Appl. No. 12/750,956 dated Jul. 16, 2013.

Russian Office Action for co-pending RU Application No. 2011144145, dated Apr. 6, 2015, with English language translation.

Japanese Office Action for co-pending JP application No. 2012-503351, dated Apr. 25, 2015, with English language translation.

Mexican Office Action for co-pending MX Application No. 2011-010311, dated Feb. 2, 2016, with English language translation.

International Search Report for PCT/PT2006/000020 dated Oct. 10, 2006.

Communication pursuant to Rules 161(1) and 162 EPC received from the EPO in co-pending application PCT/PT2010/000014, dated Nov. 25, 2011.

Communication pursuant to Article 94(3) EPC reveived from the EPO in co pending application No. 10 713 380.3-1453, dated Jul. 15, 2015.

Examiner's comments for Final Rejection in Office Action for JP 2008-162955 with English language translation.

Mexican Office Action for co-pending MX Application No. 2011-010415, dated May 12, 2015.

Russian Office Action for co-pending RU Application No. 2011144145, dated Nov. 23, 2015, with English language translation.

Communication pursuant to Article 94(3) EPC received from the EPO in co pending application No. 10 714 386.9-1460, dated Dec. 17, 2015.

Kiss, et al., "Discovery of a long-acting, peripherally selective inhibitor of a catechol-O-methyltransferase", Journal of Medicinal Chemistry, American Chemical Society, US, vol. 53, No. 8, pp. 3396-3411, Apr. 22, 2010.

Rasenack, et al., "Micron-size drug particles: common and novel micronization techniques", Pharmaceutical Development and Technology, New York, NY, US, vol. 9, No. 1, pp. 1-13, XP009055393, Jan. 1, 2004.

Dmitriyeva, et al., "Features of the reaction of some 2-chloronicotinonitriles with hydroxylamine. Synthesis of 3-(1, 2, 4-oxadiazol-3yl) pyridines and their fragmentation under electron impact". IzvestiyaVysshikh UchehnykhZavedenil, Khimiya I Khimicheskaya Teknologiya, 2005, vol. 48, No. 11, pp. 15-17, CAPLUS Abstract, DN 145:103612.

(56) References Cited

OTHER PUBLICATIONS

English language translation of Notice of Preliminary Rejection from the Korean Intellectual Property Office in co-pending Korean Patent Application No. 10-2011-7026011 dated Mar. 31, 2016.
New Examnier's Report for co-pending Canadian Patent Application No. 2,757,418 dated Apr. 11, 2016.
International Search Report and Written Opinion for PCT Application No. PCT/PT2009/000013, dated Jun. 9, 2009.
International Preliminary Report on Patentability issued in PCT/PT2009/000013, dated Sep. 21, 2010.
CMU Pharmaceutical polymorphism, Internet p. 1-3 (2002) printout Apr. 3, 2008.
Singhal et al., "Drug Polymorphism, etc.," Advanced Drug Delivery reviews 56, p. 335-347 (2004).
Concise Encyclopedia Chemistry, NY: Walter de Gruyter, 1993, 872-873.
Jain et al., "Polymorphism in Pharmacy", Indian Drugs, 1986, 23(6) 315-329.
Muzaffar et al., "Polymorphism and Drug Availability, etc.," J of Pharm. (Lahore), 1979, 1(1), 59-55.
U.S. Pharmacopia #23, National Formulary #18, 1995, 1843-1844.
Doelker, English translation of S.T.P. Pratiques (1999), 9(5), 399-409, pp. 1033.
Doelker, English translation of Ann. Pharm. Fr., 2002, 60: 161-176, pp. 1-39.
Taday et al., "Using Terahertz, etc.," J of Pharm. Sci., 92(4), 2003, 831-838.
Otuska et al., "Effect of Polymorphic, etc.," Chem. Pharm. Bull., 47(6) 852-856 (1999).

\* cited by examiner

CRYSTAL FORMS OF 5-[3-(2,5-DICHLORO-4, 6-DIMETHYL-1-OXY-PYRIDINE-3-YL)[1,2,4] OXADIAZOL-5-YL]-3-NITROBENZENE-1,2-DIOL

This is a division of application Ser. No. 12/933,044, filed Sep. 16, 2010, now U.S. Pat. No. 8,975,410, which is a National Stage Application of PCT/PT2009/000013, filed Mar. 16, 2009, which claims the benefit of priority of U.S. Provisional Application No. 61/069,721, filed Mar. 17, 2008, all of which are incorporated herein by reference.

This invention relates to novel polymorphs of 5-[3-(2,5-dichloro-4,6-dimethyl-1-oxy-pyridin-3-yl)-[1,2,4]oxadiazol-5-yl]-3-nitrobenzene-1,2-diol, an inhibitor of catechol-O-methyltransferase (COMT), to processes for their preparation, and to pharmaceutical compositions containing said novel polymorphs as active pharmaceutical ingredient.

Despite being used in clinical practice for several decades, levodopa (L-DOPA) continues to be the gold standard drug for the symptomatic treatment of Parkinson's disease. This has helped to maintain keen interest in the development of inhibitors of the enzyme catechol-O-methyltransferase (COMT) based on the hypothesis that inhibition of this enzyme may provide clinical improvements in patients afflicted by diseases such as Parkinson's disease and undergoing treatment with L-DOPA and a peripheral amino acid decarboxylase (AADC) inhibitor.

The rationale for the use of COMT inhibitors as adjuncts to L-DOPA/AADC therapy is based on their ability to reduce metabolic O-methylation of L-DOPA to 3-O-methyl-L-DOPA (3-OMD). The duration of L-DOPA induced clinical improvement is brief as a result of the short in vivo half-life of L-DOPA which contrasts with the long half-life of 3-OMD. Additionally, 3-OMD competes with L-DOPA for transport across the blood-brain barrier (BBB), which means that only a very limited amount of an orally administered dose of L-DOPA actually reaches the site of action, i.e. the brain. Commonly, within only a few years of starting L-DOPA therapy with the usual dosage regime, L-DOPA induced clinical improvement declines at the end of each dose cycle, giving rise to the so-called 'wearing-off' pattern of motor fluctuations. A close relationship between the 'wearing-off' phenomenon and accumulation of 3-OMD has been described (Tohgi, H., et al., Neurosci. Letters, 132:19-22, 1992). It has been speculated that this may result from impaired brain penetration of L-DOPA due to competition for the transport system across the BBB with 3-OMD (Reches, A. et al., Neurology, 32:887-888, 1982) or more simply that there is less L-DOPA available to reach the brain (Nutt, J. G., Fellman, J. H., Clin. Neuropharmacol., 7:35-49, 1984). In effect, COMT inhibition protects L-DOPA from metabolic breakdown in the periphery through O-methylation, such that with repeated doses of L-DOPA, the mean plasma L-DOPA concentration is raised. In addition to reduced competition for transport into the brain, a significantly greater percentage of the orally administered dose of L-DOPA is able to reach the site of action. Thus, COMT inhibition serves to increase the bioavailability of L-DOPA and therefore the duration of antiparkinsonian action is prolonged with single doses of L-DOPA (Nutt, J. G., Lancet, 351:1221-1222, 1998).

5-[3-(2,5-dichloro-4,6-dimethyl-1-oxy-pyridin-3-yl)-[1,2,4]oxadiazol-5-yl]-3-nitrobenzene-1,2-diol is a COMT inhibitor exhibiting an exceptionally long duration of action as well as balanced properties of bioactivity, bioavailability and safety. It markedly enhances the bioavailability of L-DOPA, increases the delivery of L-DOPA to the brain and significantly augments the levels of dopamine in the brain over extended periods of time.

As such, 5-[3-(2,5-dichloro-4,6-dimethyl-1-oxy-pyridin-3-yl)-[1,2,4]oxadiazol-5-yl]-3-nitrobenzene-1,2-diol is a promising candidate for treating a subject afflicted by a central or peripheral nervous system disorder, in particular for treating mood disorders, movement disorders such as Parkinson's disease and parkinsonian disorders and restless leg syndrome, gastrointestinal disturbances, oedema formation states and hypertension.

Methods of preparing 5-[3-(2,5-dichloro-4,6-dimethyl-1-oxy-pyridin-3-yl)-[1,2,4]oxadiazol-5-yl]-3-nitrobenzene-1,2-diol are described in WO2007/013830 A1.

The ability of a substance, for example 5-[3-(2,5-dichloro-4,6-dimethyl-1-oxy-pyridin-3-yl)-[1,2,4]oxadiazol-5-yl]-3-nitrobenzene-1,2-diol, to exist in more than one crystalline form is defined as polymorphism and these different crystalline forms may be referred to as "polymorphic modifications" or "polymorphs". For the purposes of this specification, the term 'polymorph' may also encompass pseudo-polymorphs. In general, polymorphism is caused by the ability of the molecule of a substance to change its conformation or to form different intermolecular and intramolecular interactions, particularly hydrogen bonds, resulting in different atomic arrangements in the crystal lattices of the different polymorphs. The polymorphs of a substance possess different crystal lattice energies and, thus, also exhibit different solid state physical properties such as morphology, density, melting point, colour, stability, dissolution rate, milling facility, granulation properties, compacting properties etc.

There are a number of processes for characterizing polymorphs. State of the art technologies include X-ray-based technologies such as X-ray powder diffraction, single crystal X-ray diffraction, microscopy, differential scanning calorimetry, and spectroscopic methods such as IR, near-IR (NIR), Raman and solid state NMR.

In pharmaceutical compositions, the use of different polymorphs often influences factors such as the preparation of pharmaceutical compositions, their stability, dissolution properties, bioavailability and, consequently, their action. In other words, the use of polymorphs allows modulation of the performance of an active pharmaceutical ingredient (API) such as 5-[3-(2,5-dichloro-4,6-dimethyl-1-oxy-pyridin-3-yl)-[1,2,4]oxa-diazol-5-yl]-3-nitrobenzene-1,2-diol as well as affecting the formulation of the API.

Accordingly, it is the object of the present invention to provide novel polymorphs of 5-[3-(2,5-dichloro-4,6-dimethyl-1-oxy-pyridin-3-yl)-[1,2,4]oxadiazol-5-yl]-3-nitrobenzene-1,2-diol.

The present invention not only relates to the provision of novel polymorphs of 5-[3-(2,5-dichloro-4,6-dimethyl-1-oxy-pyridin-3-yl)-[1,2,4]oxadiazol-5-yl]-3-nitrobenzene-1,2-diol (henceforth referred to as "compound of the invention"), but also to processes for their preparation, and to pharmaceutical compositions containing one or more of said novel polymorphs as active ingredient.

In one embodiment, the present invention relates to a polymorph of the compound of the invention which is, in the following specification, referred to as polymorph A. A process for the preparation of polymorph A is given in the experimental section. Polymorph A is a crystalline polymorph and, thus, characterizable by its powder X-ray diffraction pattern (XRPD). The diffraction pattern may either be experimentally recorded or calculated from the results of the measurement of the unit cell parameters of the polymorph. In the following, characteristic peaks of the XRPDs of the polymorphs of the invention are given in degrees 2θ (Cu—Kα radiation).

Polymorph A is characterizable by one or more of the peaks given in the following table.

TABLE 1

| XRPD of polymorph A | |
|---|---|
| Peak Position (°2θ) | Rel. Intensity (%) |
| 6.6 | 55 |
| 6.9 | 9 |
| 11.8 | 40 |
| 13.2 | 100 |
| 17.2 | 8 |
| 17.9 | 33 |
| 19.8 | 25 |
| 22.6 | 12 |
| 23.2 | 71 |
| 23.8 | 74 |
| 24.3 | 36 |
| 25.3 | 53 |
| 25.9 | 42 |
| 26.4 | 45 |
| 27.8 | 11 |
| 28.2 | 36 |
| 28.6 | 29 |
| 29.6 | 16 |
| 29.9 | 20 |
| 30.3 | 11 |
| 30.7 | 14 |
| 32.0 | 5 |
| 32.7 | 14 |
| 33.5 | 6 |
| 34.1 | 6 |
| 35.1 | 9 |
| 36.5 | 9 |
| 37.0 | 8 |
| 37.6 | 4 |
| 39.2 | 5 |

Preferably, polymorph A is characterized by one or more of the above peaks in the range of from about 5 to about 25°/2θ which is a highly characteristic region of XRPDs. More preferably, polymorph A is characterized by 2 to 10, preferably 3 to 5, peaks within the range of from about 5 to about 25°/2θ. Even more preferably, the polymorph A is characterized by the signals at 6.6, 13.2, 17.9, 23.2, 23.8 and 24.3°/2θ. Most preferably, polymorph A is characterized by the signals at 6.6, 13.2, 17.9 and 23.8°/2θ.

One skilled in the art will recognize that the 2θ degrees given above will generally be reproducible to within a range from about ±0.10 2θ degrees to about ±0.20 2θ degrees, with a preferred range being ±0.10 2θ degrees. See e.g. United States Pharmacopoeia XXV (2002), p. 2088-2089. This also applies to other XRPD data given in this specification.

In addition, polymorph A may also be characterizable by having an exotherm at 251° C. in a Differential Scanning calorimetry (DSC) thermogram.

One skilled in the art will recognize that the exotherm given above will generally be reproducible to within a range from about ±0.5 to 3° C., preferably ±2° C., more preferably ±1° C., and most preferably ±0.5° C. This also applies to other DSC and also the melt-onset of hot stage data given in this specification.

Hotstage analysis also indicates that polymorph A may also be characterised by exhibiting a melt onset at 238° C.

Furthermore, polymorph A may also be characterized by being non-hygroscopic over the range of about 5% to about 95%, more preferably from about 25% to about 80%, and even more preferably from about 40% to about 60%, relative humidity at 25° C. over a period of 3 months.

In addition, polymorph A is preferably an anhydrate as is evidenced by a lack of solvent desorption in combined Differential Scanning calorimetry (DSC) and Thermogravimetric Analysis (TGA) experiments prior to energetic decomposition.

Polymorph A is also characterizable by one or more of the following FT-Raman Peak Positions:

TABLE 2

| Raman spectra of polymorph A | |
|---|---|
| Peak position (cm$^{-1}$) | Rel. Intensity (%) |
| 145 | 35 |
| 170 | 22 |
| 216 | 22 |
| 237 | 16 |
| 256 | 23 |
| 285 | 14 |
| 339 | 27 |
| 370 | 24 |
| 420 | 14 |
| 442 | 12 |
| 465 | 14 |
| 505 | 37 |
| 526 | 19 |
| 710 | 11 |
| 810 | 43 |
| 974 | 10 |
| 1007 | 14 |
| 1059 | 16 |
| 1159 | 40 |
| 1228 | 38 |
| 1254 | 23 |
| 1277 | 23 |
| 1325 | 44 |
| 1387 | 30 |
| 1414 | 32 |
| 1448 | 25 |
| 1498 | 23 |
| 1537 | 63 |
| 1589 | 100 |
| 1628 | 50 |
| 2927 | 17 |

Preferably, polymorph A is characterizable by one or more, preferably 2 to 6, and more preferably 3 to 5, peak positions in the above table. More preferably, polymorph A is characterized by one or more of the peaks at 145, 505, 810, 1159, 1228, 1325, 1537, 1589, and 1628 cm$^{-1}$. Most preferably, polymorph A is characterized by the peaks at 810, 1325, 1537, 1589, and 1628 cm$^{-1}$.

One skilled in the art will recognize that the FT-Raman Peak Positions will generally be reproducible within a range from about ±0 cm$^{-1}$ to ±5 cm$^{-1}$, preferably from ±1 cm$^{-1}$ to ∓3 cm$^{-1}$, most preferably ±2 cm$^{-1}$. This also applies to the other Raman data presented in this specification.

Polymorph A is also characterizable by one or more of the following peak positions in Solid State 13C-NMR:

TABLE 3

| Solid State 13C-NMR of polymorph A |
|---|
| Peak position (ppm) |
| 174.0 |
| 163.9 |
| 150.4 |
| 148.8 |
| 144.5 |
| 140.2 |

TABLE 3-continued

Solid State 13C-NMR of polymorph A
Peak position (ppm)

| |
|---|
| 134.8 |
| 133.2 |
| 129.8 |
| 124.9 |
| 124.0 |
| 122.1 |
| 114.6 |
| 22.5 |
| 15.7 |

Preferably, polymorph A is characterizable by one or more, preferably 2 to 6, and more preferably 3 to 5, peak positions in the above table. Most preferably, polymorph A is characterized by the peaks at 15.7, 114.6, 148.8 and 174.0 ppm.

One skilled in the art will recognize that the $^{13}$C-ssNMR peaks will generally be reproducible within a range from about ±0.1 ppm to ±0.3 ppm, preferably ±0.2 ppm. This also applies to the other NMR data presented in this specification.

In another embodiment, the present invention relates to a polymorph of the compound of the invention which is, in the following specification, referred to as polymorph B. A process for the preparation of polymorph B is given in the experimental section.

Polymorph B is a crystalline polymorph and, thus, characterizable by its powder X-ray diffraction pattern (XRPD). The diffraction pattern was recorded with Cu—Kα radiation and is characterizable by one or more of the peaks given in the following table.

TABLE 4

XRPD of polymorph B

| Peak Position (°2θ) | Rel. Intensity (%) |
|---|---|
| 5.7 | 69 |
| 6.9 | 68 |
| 8.0 | 24 |
| 9.8 | 26 |
| 11.3 | 36 |
| 11.9 | 93 |
| 13.8 | 100 |
| 14.4 | 27 |
| 16.9 | 63 |
| 19.6 | 87 |
| 20.4 | 28 |

Preferably, polymorph B is characterized by one or more of the above peaks in the range of from about 5 to about 25°/2θ which is a highly characteristic region of XRPDs. More preferably, polymorph B is characterized by 2 to 10, preferably 3 to 5, peaks within the range of from about 5 to about 25/2θ. Even more preferably, the polymorph B is characterized by the signals at 5.7, 6.9, 11.9, 13.8, 16.9 and 19.6°/2θ. Most preferably, polymorph B is characterized by the signals at 5.7, 6.9, 13.8 and 19.6°/2θ.

In addition, polymorph B may also be characterizable by having an exotherm at 237° C. in a Differential Scanning calorimetry (DSC) thermogram. Such analyses may also indicate a shoulder peak at 231° C.

In addition, polymorph B is preferably an anhydrate as is evidenced by a lack of solvent desorption in combined Differential Scanning calorimetry (DSC) and Thermogravimetric Analysis (TGA) experiments prior to energetic decomposition. However, molecular packaging of polymorph B allows the accommodation of crystal water without substantially altering the crystal lattice.

Polymorph B is also characterizable by one or more of the following FT-Raman Peak Positions:

TABLE 5

Raman spectra of polymorph B

| Peak position (cm$^{-1}$) | Rel. Intensity (%) |
|---|---|
| 141 | 26 |
| 214 | 23 |
| 235 | 16 |
| 253 | 20 |
| 280 | 14 |
| 339 | 25 |
| 361 | 18 |
| 372 | 19 |
| 399 | 15 |
| 415 | 18 |
| 440 | 12 |
| 463 | 15 |
| 505 | 49 |
| 526 | 21 |
| 710 | 14 |
| 812 | 54 |
| 887 | 11 |
| 926 | 13 |
| 970 | 12 |
| 1001 | 22 |
| 1059 | 19 |
| 1157 | 10 |
| 1227 | 14 |
| 1292 | 49 |
| 1317 | 43 |
| 1385 | 50 |
| 1406 | 34 |
| 1444 | 32 |
| 1504 | 27 |
| 1537 | 44 |
| 1583 | 100 |
| 1630 | 69 |
| 2933 | 31 |

Preferably, polymorph B is characterizable by one or more, preferably 2 to 6, and more preferably 3 to 5, peak positions in the above table. More preferably, polymorph B is characterized by one or more of the peaks at 505, 1292, 1317, 1385, 1537, 1583, and 1630 cm$^{-1}$. Most preferably, polymorph B is characterized by the peaks at 505, 1292, 1385, 1583, and 1630 cm$^{-1}$.

Polymorph B is also characterizable by one or more of the following peak positions in Solid State $^{13}$C-NMR:

TABLE 6

Solid State 13C-NMR of polymorph B
Peak positions (ppm)

| |
|---|
| 174.4 |
| 164.7 |
| 150.3 |
| 139.1 |
| 133.9 |
| 132.8 |
| 123.5 |
| 120.3 |
| 114.0 |
| 112.6 |
| 19.8 |
| 16.6 |

Preferably, polymorph B is characterizable by one or more, preferably 2 to 6, and more preferably 3 to 5, peak positions in the above table. Most preferably, polymorph B is characterized by the peaks at 150.3, 133.9, 112.6 and 19.8 ppm.

In yet another embodiment, the present invention relates to a polymorph of the compound of the invention which is, in the following specification, referred to as polymorph C. A process for the preparation of polymorph C is given in the experimental section.

Polymorph C is a crystalline polymorph and, thus, characterizable by one or more of the peaks of its powder X-ray diffraction pattern (XRPD). The diffraction pattern was recorded with Cu—Kα radiation and is given in the following table.

TABLE 7

XRPD of polymorph C

| Peak Position (°2θ) | Rel. Intensity (%) |
| --- | --- |
| 4.9 | 100 |
| 7.3 | 22 |
| 9.5 | 13 |
| 9.9 | 8 |
| 10.3 | 10 |
| 13.3 | 61 |
| 13.8 | 6 |
| 14.5 | 13 |
| 17.2 | 8 |
| 18.0 | 19 |
| 19.1 | 34 |
| 19.9 | 13 |
| 20.7 | 19 |
| 21.9 | 5 |
| 22.6 | 21 |
| 23.4 | 11 |
| 24.0 | 44 |
| 24.6 | 16 |
| 24.9 | 31 |
| 25.3 | 24 |
| 25.8 | 8 |
| 26.7 | 25 |
| 27.2 | 16 |
| 27.6 | 8 |
| 28.4 | 23 |
| 28.8 | 9 |
| 29.3 | 11 |
| 29.9 | 5 |
| 30.5 | 5 |
| 31.8 | 8 |
| 32.8 | 8 |
| 33.9 | 6 |
| 34.6 | 5 |
| 35.4 | 5 |
| 35.8 | 5 |
| 36.6 | 5 |
| 37.6 | 5 |
| 38.2 | 3 |
| 38.7 | 6 |

Preferably, polymorph C is characterized by one or more of the above peaks in the range of from about 5 to about 25°/2θ which is a highly characteristic region of XRPDs. More preferably, polymorph C is characterized by 2 to 10, preferably 3 to 5, peaks within the range of from about 5 to about 25°/2θ. Even more preferably, the polymorph C is characterized by the signals at 4.9, 7.3, 13.3, 19.1, 21.9, 23.4 and 24.0°/2θ. Most preferably, polymorph C is characterized by the signals at 4.9, 13.3, 19.1 and 24.0°/2θ.

Polymorph C may also be characterised by showing an exotherm at 203° C. in a Differential Scanning calorimetry (DSC) thermogram.

Polymorph C is also characterizable by one or more of the following FT-Raman Peak Positions:

TABLE 8

Raman spectra of polymorph C

| Peak position (cm$^{-1}$) | Rel. Intensity (%) |
| --- | --- |
| 143 | 38 |
| 214 | 19 |
| 237 | 14 |
| 253 | 17 |
| 282 | 14 |
| 299 | 13 |
| 339 | 30 |
| 370 | 20 |
| 401 | 13 |
| 418 | 14 |
| 444 | 10 |
| 465 | 12 |
| 507 | 40 |
| 530 | 15 |
| 667 | 13 |
| 710 | 14 |
| 739 | 11 |
| 810 | 41 |
| 972 | 11 |
| 1003 | 14 |
| 1061 | 20 |
| 1147 | 21 |
| 1244 | 42 |
| 1281 | 34 |
| 1317 | 36 |
| 1352 | 36 |
| 1387 | 55 |
| 1406 | 45 |
| 1450 | 30 |
| 1483 | 22 |
| 1506 | 24 |
| 1537 | 42 |
| 1585 | 100 |
| 1630 | 59 |
| 2918 | 15 |

Preferably, polymorph C is characterizable by one or more, preferably 2 to 6, and more preferably 3 to 5, peak positions in the above table. More preferably, polymorph C is characterized by one or more of the peaks at 143, 507, 810, 1244, 1281, 1317, 1352, 1387, 1406, 1537, 1585, and 1630 cm$^{-1}$. Most preferably, polymorph C is characterized by the peaks at 1387, 1406, 1537, 1585, and 1630 cm$^{-1}$.

Polymorph C is also characterizable by one or more of the following peak positions in Solid State $^{13}$C-ssNMR:

TABLE 9

Solid State 13C-NMR of polymorph C
Peak positions (ppm)

| |
| --- |
| 173.9 |
| 165.0 |
| 150.7 |
| 141.0 |
| 138.6 |
| 133.5 |
| 122.8 |
| 120.3 |
| 114.0 |
| 112.4 |
| 41.1 |
| 20.2 |
| 17.9 |

Preferably, polymorph C is characterizable by one or more, preferably 2 to 6, and more preferably 3 to 5, peak positions in the above table. Most preferably, polymorph C is characterized by the peaks at 150.7, 133.5, 114.0 and 20.2 ppm.

In yet another embodiment, the present invention relates to a polymorph of the compound of the invention which is, in the following specification, referred to as polymorph D. A process for the preparation of polymorph D is given in the experimental section.

Polymorph D is a crystalline polymorph and, thus, characterizable by one or more of the peaks of its powder X-ray diffraction pattern (XRPD). The diffraction pattern was recorded with Cu—Kα radiation and is given in the following table.

TABLE 10

XRPD of polymorph D

| Peak Position (°2θ) | Rel. Intensity (%) |
|---|---|
| 11.6 | 21 |
| 12.3 | 23 |
| 20.0 | 43 |
| 20.7 | 100 |
| 21.4 | 69 |
| 23.8 | 25 |
| 24.8 | 26 |
| 26.6 | 11 |
| 27.4 | 12 |
| 28.0 | 12 |
| 29.1 | 31 |
| 31.1 | 56 |
| 32.0 | 20 |
| 33.3 | 39 |
| 35.0 | 23 |
| 36.0 | 35 |

Preferably, polymorph D is characterized by one or more of the above peaks in the range of from about 5 to about 25°/2θ which is a highly characteristic region of XRPDs. More preferably, polymorph D is characterized by 2 to 10, preferably 3 to 5, peaks within the range of from about 5 to about 25°/2θ. Even more preferably, the polymorph D is characterized by the signals at 11.6, 12.3, 20.0, 20.7, 21.4 and 24.8°/2θ. Most preferably, polymorph D is characterized by the signals at 12.3, 20.0, 20.7 and 21.4°/2θ.

In yet another embodiment, the present invention relates to a polymorph of the compound of the invention which is, in the following specification, referred to as polymorph E. A process for the preparation of polymorph E is given in the experimental section.

Polymorph E is a crystalline polymorph and, thus, characterizable by one or more of the peaks of its powder X-ray diffraction pattern (XRPD). The diffraction pattern was recorded with Cu—Kα radiation and is given in the following table.

TABLE 11

XRPD of polymorph E

| Peak Position (°2θ) | Rel. Intensity (%) |
|---|---|
| 4.5 | 8 |
| 5.4 | 34 |
| 6.2 | 36 |
| 6.9 | 4 |
| 7.8 | 52 |
| 8.4 | 3 |
| 9.8 | 100 |
| 10.8 | 89 |
| 11.2 | 69 |
| 11.5 | 11 |
| 12.2 | 87 |
| 12.4 | 31 |
| 13.8 | 22 |
| 14.6 | 44 |
| 15.6 | 16 |
| 16.2 | 4 |
| 17.1 | 5 |
| 17.6 | 15 |
| 18.7 | 30 |
| 19.8 | 48 |
| 20.1 | 37 |
| 21.7 | 8 |
| 22.6 | 21 |
| 22.9 | 26 |
| 24.0 | 16 |
| 24.5 | 30 |
| 25.1 | 16 |
| 26.0 | 81 |
| 27.3 | 68 |
| 28.8 | 13 |
| 30.6 | 9 |
| 31.5 | 11 |
| 32.7 | 8 |
| 33.5 | 20 |
| 34.1 | 21 |
| 35.8 | 8 |
| 36.9 | 9 |
| 39.2 | 7 |

Preferably, polymorph E is characterized by one or more of the above peaks in the range of from about 5 to about 25°/2θ which is a highly characteristic region of XRPDs. More preferably, polymorph E is characterized by 2 to 10, preferably 3 to 5, peaks within the range of from about 5 to about 25°/2θ. Even more preferably, the polymorph E is characterized by the signals at 7.8, 9.8, 12.2, 15.6, 16.2, 17.6, 19.8, 21.7, 22.9, and 24.5°/2θ. Most preferably, polymorph E is characterized by the signals at 9.8, 11.2, 19.8 and 24.5°/2θ.

Polymorph E may be further characterised by showing an endotherm at 159° C. in a Differential Scanning calorimetry (DSC) thermogram. Polymorph E may be even further characterised by showing an exotherm at 243° C. in a Differential Scanning calorimetry (DSC) thermogram.

Polymorph E is also characterizable by one or more of the following FT-Raman Peak Positions:

TABLE 12

Raman spectra of polymorph E

| Peak position (cm$^{-1}$) | Rel. Intensity (%) |
|---|---|
| 127 | 58 |
| 216 | 16 |
| 231 | 17 |
| 260 | 16 |
| 341 | 21 |
| 384 | 20 |
| 461 | 15 |
| 498 | 20 |
| 526 | 14 |
| 712 | 13 |
| 739 | 26 |
| 769 | 10 |
| 816 | 19 |
| 893 | 15 |
| 922 | 19 |
| 972 | 17 |

TABLE 12-continued

Raman spectra of polymorph E

| Peak position (cm$^{-1}$) | Rel. Intensity (%) |
|---|---|
| 1005 | 27 |
| 1022 | 45 |
| 1057 | 17 |
| 1174 | 15 |
| 1209 | 23 |
| 1234 | 31 |
| 1269 | 34 |
| 1288 | 33 |
| 1327 | 35 |
| 1356 | 100 |
| 1412 | 35 |
| 1460 | 29 |
| 1506 | 31 |
| 1533 | 52 |
| 1556 | 58 |
| 1583 | 97 |
| 1635 | 79 |
| 2931 | 11 |

Preferably, polymorph E is characterizable by one or more, preferably 2 to 6, and more preferably 3 to 5, peak positions in the above table. More preferably, polymorph E is characterized by one or more of the peaks at 127, 1022, 1269, 1288, 1327, 1356, 1412, 1533, 1556, 1583, and 1635 cm$^{-1}$. Most preferably, polymorph E is characterized by the peaks at 1356, 1533, 1556, 1583, and 1635 cm$^{-1}$.

Polymorph E is also characterizable by one or more of the following peak positions in Solid State 13C-NMR:

TABLE 13

Solid State $^{13}$C-NMR of polymorph E
Peak Positions (ppm)

| |
|---|
| 175.2 |
| 164.2 |
| 158.8 |
| 151.8 |
| 147.1 |
| 145.5 |
| 143.4 |
| 139.4 |
| 136.4 |
| 133.6 |
| 130.7 |
| 127.3 |
| 124.8 |
| 123.3 |
| 118.1 |
| 108.3 |
| 105.1 |
| 19.4 |
| 17.6 |

Preferably, polymorph E is characterizable by one or more, preferably 2 to 6, and more preferably 3 to 5, peak positions in the above table. Most preferably, polymorph C is characterized by the peaks at 151.8, 133.6, 105.1 and 19.4 ppm.

In yet another embodiment, the present invention relates to a polymorph of the compound of the invention which is, in the following specification, referred to as polymorph F. A process for the preparation of polymorph F is given in the experimental section.

Polymorph F is a crystalline polymorph and, thus, characterizable by one or more of the peaks of its powder X-ray diffraction pattern (XRPD). The diffraction pattern was recorded with Cu—Kα radiation and is given in the following table.

TABLE 14

XRPD of polymorph F

| Peak Position (°2θ) | Rel. Intensity (%) |
|---|---|
| 4.9 | 62 |
| 6.3 | 64 |
| 8.2 | 80 |
| 10.7 | 81 |
| 11.4 | 58 |
| 12.6 | 65 |
| 13.5 | 59 |
| 14.4 | 49 |
| 16.4 | 58 |
| 18.8 | 55 |
| 20.5 | 56 |
| 21.5 | 66 |
| 23.9 | 58 |
| 24.8 | 65 |
| 25.4 | 100 |
| 26.4 | 46 |
| 27.5 | 57 |
| 28.5 | 42 |
| 29.7 | 42 |
| 33.2 | 33 |
| 34.7 | 28 |

Preferably, polymorph F is characterized by one or more of the above peaks in the range of from about 5 to about 25°/2θ which is a highly characteristic region of XRPDs. More preferably, polymorph F is characterized by 2 to 10, preferably 3 to 5, peaks within the range of from about 5 to about 25°/2θ. Even more preferably, the polymorph F is characterized by the signals at 8.2, 10.7, 12.6, 13.5, 16.4 and 25.4°/2θ. Most preferably, polymorph F is characterized by the signals at 10.7, 12.6, 16.4 and 25.4°/2θ.

In interconversion experiments, it was found that the polymorphs C, D, E, and F convert into polymorph A or B, i.e. modifications A and B are kinetically stable polymorphs. Furthermore, it was found that polymorph B converts into polymorph A when slurried in water containing crystal seeds of modification A over prolonged periods of time. Thus, polymorph A is the thermodynamically stable polymorph.

In particular, drying of polymorph C under vacuum at ambient temperature or at 60° C. produced polymorph B, and drying of polymorph E under vacuum at ambient temperature or at 60° C. produced polymorph A.

Given the fact that modifications A and B are thermodynamically stable and kinetically stable, respectively, they will in particular be characterized by good storage stability. Storage stability of the polymorph is defined herein as a lack of rearrangement of one polymorphic modification into another modification under storage conditions of 60% relative humidity and 25° C. over a period of 3 months. Accordingly, physical parameters related to the polymorphic modification such as the XRPD, Raman spectra and the Differential Scanning calorimetry (DSC) thermogram will not change upon storage under the above-specified conditions.

Furthermore, these polymorphs will also exhibit stable dissolution properties as these properties are dependent on the above defined storage stability of the polymorph. Accordingly, the modifications A and B are also characterized in that they will not be subject to a change in their dissolution profile upon storage. A lack of change in the dissolution profile is defined herein as a variation of the time period until 80% of the polymorph has dissolved under test conditions according to the USP Paddle Test Method, USP, 30th Edition, The National Formulary 25th Edition, 2007, The United States Pharmacopeial Convention, Rockville, volume 1, chapter 711, of less than 10%, preferably less than 5% and most preferably less than 1%, after storage under conditions of 60% relative humidity at 25° C. over a period of at least 3 months.

The polymorphs of the present invention may be used as active pharmaceutical ingredients in pharmaceutical formulations such as tablets, capsules or injections, without or in combination with one or more pharmaceutically acceptable additives such as sugar, starch, starch derivatives, cellulose, cellulose derivatives, release agents, anti-adhesive agents and agents for regulating flowability.

With regard to pharmaceutical formulations comprising polymorph A the present invention also relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that the X-ray powder diffractogram of the composition exhibits one or more, preferably 1 to 6, more preferably 2 to 4, and most preferably 3, 2θ angles from the following list of 2θ angles: 6.6, 6.9, 11.8, 13.2, 17.2, 17.9, 19.8, 22.6, 23.2, 23.8, 24.3, and 25.3. Preferably, said formulation is characterized by an XRPD having one or more of the following characteristic peaks for polymorph A: 6.6, 23.2 and 24.3.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 145, 170, 216, 237, 256, 285, 339, 370, 420, 442, 465, 505, 526, 710, 810, 974, 1007, 1059, 1159, 1228, 1254, 1277, 1325, 1387, 1414, 1448, 1498, 1537, 1589, 1628, 2927.

Furthermore, said pharmaceutical composition may also be further characterized in that its Solid State 13C-NMR spectrum (100 MHz) exhibits at least one, preferably 1 to 6, more preferably 2 to 4, and most preferably 3, peaks from the following peak list [ppm]: 174.0, 163.9, 150.4, 148.8, 144.5, 140.2, 134.8, 133.2, 129.8, 124.9, 124.0, 122.1, 114.6, 22.5, and 15.7.

The pharmaceutical formulations comprising polymorph A may also exhibit an exotherm at 251° C. in a Differential Scanning calorimetry (DSC) thermogram.

In an alternative embodiment, with regard to pharmaceutical formulations comprising polymorph B, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 1 to 6, more preferably 2 to 4, and most preferably 3, 2θ angles from the following list of 2θ angles: 5.7, 6.9, 8.0, 9.8, 11.3, 11.9, 13.8, 14.4, 16.9, 19.6, and 20.4. Preferably, said formulation is characterized by an XRPD having one or more of the following characteristic peaks for polymorph B: 5.7, 16.9 and 19.6.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 141, 214, 235, 253, 280, 339, 361, 372, 399, 415, 440, 463, 505, 526, 710, 812, 887, 926, 970, 1001, 1059, 1157, 1227, 1292, 1317, 1385, 1406, 1444, 1504, 1537, 1583, 1630, and 2933.

Furthermore, said pharmaceutical composition may also be further characterized in that its Solid State 13C-NMR spectrum (100 MHz) exhibits at least one, preferably 1 to 6, more preferably 2 to 4, and most preferably 3, peaks from the following peak list [ppm]: 174.4, 164.7, 150.3, 139.1, 133.9, 132.8, 123.5, 120.3, 114.0, 112.6, 19.8, and 16.6.

The pharmaceutical formulations comprising polymorph B may also exhibit an exotherm at 237° C., in a Differential Scanning calorimetry (DSC) thermogram.

In an alternative embodiment, with regard to pharmaceutical formulations comprising polymorph C, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 1 to 6, more preferably 2 to 4, and most preferably 3, 2θ angles from the following list of 2θ: 4.9, 7.3, 9.5, 9.9, 10.3, 13.3, 13.8, 14.5, 17.2, 18.0, 19.1, 19.9, 20.7, 21.9, 22.6, 23.4, 24.0, 24.6, 24.9, and 25.3. Preferably, said formulation is characterized by an XRPD having one or more of the following characteristic peaks for polymorph C: 7.3, 19.1, 21.9 and 23.4.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 143, 214, 237, 253, 282, 299, 339, 370, 401, 418, 444, 465, 507, 530, 667, 710, 739, 810, 972, 1003, 1061, 1147, 1244, 1281, 1317, 1352, 1387, 1406, 1450, 1483, 1506, 1537, 1585, 1630, and 2918.

Furthermore, said pharmaceutical composition may also be further characterized in that its Solid State 13C-NMR spectrum (100 MHz) exhibits at least one, preferably 1 to 6, more preferably 2 to 4, and most preferably 3, peaks from the following peak list [ppm]: 173.9, 165.0, 150.7, 141.0, 138.6, 133.5, 122.8, 120.3, 114.0, 112.4, 41.1, 20.2, and 17.9.

The pharmaceutical formulations comprising polymorph C may also exhibit an exotherm at 203° C. in a Differential Scanning calorimetry (DSC) thermogram.

In an alternative embodiment, with regard to pharmaceutical formulations comprising polymorph D, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 2 to 10, more preferably 3 to 5, and most preferably 4, 2θ angles from the following list of 2θ angles: 11.6, 12.3, 20.0, 20.7, 21.4, 23.8, 24.8, 26.6, 27.4, 28.0, 29.1, 31.1, 32.0, 33.3, 35.0, and 36.0.

In an alternative embodiment, with regard to pharmaceutical formulations comprising polymorph E, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 1 to 6, more preferably 2 to 4, and most preferably 3, 2θ angles from the following list of 2θ angles: 4.5, 5.4, 6.2, 6.9, 7.8, 8.4, 9.8, 10.8, 11.2, 11.5, 12.2, 12.4, 13.8, 14.6, 15.6, 16.2, 17.1, 17.6, 18.7, 19.8, 20.1, 21.7, 22.6, 22.9, 24.0, 24.5, 25.1, 26.0, 27.3, 28.8, 30.6, 31.5, 32.7, 33.5, 34.1, 35.8, 36.9, and 39.2. Preferably, said formulation is characterized by an XRPD having one or more of the following characteristic peaks for polymorph E: 7.8, 15.6, 16.2, 17.6, 21.7 and 22.9.

Furthermore, said pharmaceutical composition may further be characterized in that its Raman spectrum exhibits at least one, preferably 1 to 6, more preferably 2 to 4, and most preferably 3, peaks from the following peak list [cm$^{-1}$]: 127, 216, 231, 260, 341, 384, 461, 498, 526, 712, 739, 769, 816, 893, 922, 972, 1005, 1022, 1057, 1174, 1209, 1234, 1269, 1288, 1327, 1356, 1412, 1460, 1506, 1533, 1556, 1583, 1635, and 2931.

Furthermore, said pharmaceutical composition may also be further characterized in that its Solid State 13C-NMR spectrum (100 MHz) exhibits at least one, preferably 2 to 10, more preferably 3 to 5, and most preferably 4, peaks from the following peak list [ppm]: 175.2, 164.2, 158.8, 151.8, 147.1, 145.5, 143.4, 139.4, 136.4, 133.6, 130.7, 127.3, 124.8, 123.3, 118.1, 108.3, 105.1, 19.4, and 17.6.

The pharmaceutical formulations comprising polymorph E may also exhibit an exotherm at 243° C. in a Differential Scanning calorimetry (DSC) thermogram.

In an alternative embodiment, with regard to pharmaceutical formulations comprising polymorph F, the present invention relates to a pharmaceutical composition, characterized in that it comprises 5-[3-(2,5-dichloro-4,6-dimethyl-1-oxy-pyridin-3-yl)-[1,2,4]oxadiazol-5-yl]-3-nitrobenzene-1,2-diol and that its X-ray powder diffractogram exhibits one or more, preferably 2 to 10, more preferably 3 to 5, and most preferably 4, 2θ angles from the following list of 2θ angles: 4.9, 6.3, 8.2, 10.7, 11.4, 12.6, 13.5, 14.4, 16.4, 18.8, 20.5, 21.5, 23.9, 24.8, 25.4, 26.4, 27.5, 28.5, 29.7, 33.2, and 34.7. Preferably, said formulation is characterized by an XRPD having one or more of the following characteristic peaks for polymorph F: 8.2, 12.6, 13.5, and 16.4.

When properly formulated by the skilled person, the physical properties of the polymorphs are reflected in the pharmaceutical formulations. Accordingly, pharmaceutical formulations comprising the stable polymorphs A and/or B will also be storage stable. Thus, pharmaceutical formulations containing modifications A and/or B are further characterized in that they will not be subject to a change in their dissolution profile upon storage. A lack of change in the dissolution profile is defined herein as a lack of variation of the time period until 80% of the active pharmaceutical ingredient has been released under test conditions according to the USP Paddle Test Method, USP, 30th Edition, The National Formulary 25th Edition, 2001, The United States Pharmacopeial Convention, Rockville, volume 1, chapter 711, of less than 10%, preferably less than 5% and most preferably less than 1%, after storage under conditions of 60% relative humidity at 25° C. over a period of at least 3 months.

Furthermore, the stability of modifications A and B can be used to convert metastable modifications such as modifications C to F into the more stable modifications A or B. Likewise, due to the stability of modifications A and B, mixtures of metastable modifications can be converted to polymorphically pure modifications A and B e.g. by seeding slurries of such mixtures with modification A or B. Modification B can also be converted to modification A e.g. by seeding a slurry of modification B with seeding crystals of modification A.

It is particularly preferred to convert modifications less stable than modification A such as amorphic, metastable and polymorphically impure modifications to the thermodynamically most stable modification A. The most preferred process for doing so is seeding such modifications or mixtures of modifications with seeding crystals of modification A. Another preferred process for achieving a conversion is the dissolution of said modifications, followed by seeding with crystals of modification A.

EXPERIMENTAL SECTION

Process for the Preparation of Polymorph A

A 1600 L reactor was charged with 245 kg formic acid and 10 kg 5-[3-(2,5-dichloro-4,6-dimethyl-1-oxy-pyridin-3-yl)-[1,2,4]oxadiazol-5-yl]-3-nitrobenzene-1,2-diol. The mixture was heated to 70-75° C. until the solid dissolved. The hot solution was then filtered to a 250 L reactor, and then cooled to 25-35° C. Vacuum was applied and the mixture was distilled at 50° C. until 50-70 liters remained. To this mixture 160 kg isopropanol was introduced. The mixture was cooled to 5-10° C. and was allowed to stir for 10 hours. The suspension was then centrifuged and washed with 13 kg isopropanol. The wet material was removed from the centrifuge and dried in a vacuum tray drier. The dried material weight was 8.995 kg after sampling. The yield of polymorph A was 9.395 kg, 93.9%.

Process for the Preparation of Polymorph B 161.6 mg of 5-[3-(2,5-dichloro-4,6-dimethyl-1-oxy-pyridin-3-yl)-[1,2,4]oxadiazol-5-yl]-3-nitrobenzene-1,2-diol were added to a glass vial. Formic acid (2.0 mL) was added and the sample warmed to 73° C. in an oil bath. The resulting mixture was filtered though a 0.2 μm nylon filter into a clean vial at room temperature. Solids of polymorph B were precipitated via addition of water (2.0 mL) and were collected by filtration.

Process for the Preparation of Polymorph C 161.0 mg of 5-[3-(2,5-dichloro-4,6-dimethyl-1-oxy-pyridin-3-yl)-[1,2,4]oxadiazol-5-yl]-3-nitrobenzene-1,2-diol were added to a glass vial and dissolved in DMSO (4.0 mL). The solution was filtered through a 0.2 μm nylon filter into a clean vial and evaporated to dryness in a centrifugal evaporator set at 50° C. under vacuum to yield polymorph C.

Process for the Preparation of Polymorph D

A saturated solution of 5-[3-(2,5-dichloro-4,6-dimethyl-1-oxy-pyridin-3-yl)-[1,2,4]oxadiazol-5-yl]-3-nitrobenzene-1,2-diol was generated in a 1:1 dioxane:water mixture (1.0 mL). The resulting mixture was filtered through a 0.2 μm nylon filter into a clean vial and evaporated to dryness under ambient conditions to yield polymorph D.

Process for the Preparation of Polymorph E 151.2 mg of 5-[3-(2,5-dichloro-4,6-dimethyl-1-oxy-pyridin-3-yl)-[1,2,4]oxadiazol-5-yl]-3-nitrobenzene-1,2-diol were added to a glass vial and dissolved in pyridine (3.0 mL). The solution was filtered through a 0.2 μm nylon filter into a clean vial and evaporated to dryness under a nitrogen stream yielding polymorph E.

Process for the Preparation of Polymorph F

A saturated solution of 5-[3-(2,5-dichloro-4,6-dimethyl-1-oxy-pyridin-3-yl)-[1,2,4]oxadiazol-5-yl]-3-nitrobenzene-1,2-diol was generated in DMSO (0.500 mL). The resulting mixture was filtered through a 0.2 μm nylon filter into a clean vial. Approximately 60 μL of this solution was dispensed into a capillary. The capillary was placed into a centrifugal evaporator at ambient temperature and the solvent removed under reduced pressure yielding polymorph F.

Analysis was performed with the following instrumentation:
1. PANalytical X'Pert Pro Diffractometer
   Samples of polymorphs A, C and E were analyzed using a PANalytical X'Pert Pro diffractometer. The specimen was analyzed using Cu radiation produced using an Optix long fine-focus source. An elliptically graded multilayer mirror was used to focus the Cu Kα X-rays of the source through the specimen and onto the detector. The specimen was sandwiched between 3-micron thick films, analyzed in transmission geometry, and rotated to optimize orientation statistics. A beam-stop and helium were used to minimize the background generated by air scattering. Soller slits were used for the incident and diffracted beams to minimize axial divergence. Diffraction patterns were collected using a scanning position-sensitive detector (X'Celerator) located 240 mm from the specimen. The data-acquisition parameters of each diffraction pattern are displayed above the image of each pattern in appendix data section. Prior to the analysis a silicon specimen (NIST standard reference material 640c) was analyzed to verify the position of the silicon 111 peak.

2. Shimadzu XRD-6000 Diffractometer

Samples of polymorph B were analyzed using a Shimadzu XRD-6000 X-ray powder diffractometer using Cu Kα radiation. The instrument is equipped with a long fine focus X-ray tube. The tube voltage and amperage were set at 40 kV and 40 mA, respectively. The divergence and scattering slits were set at 1° and the receiving slit was set at 0.15 mm. Diffracted radiation was detected by a NaI scintillation detector. A theta-two theta continuous scan at 3°/min (0.4 sec/0.02° step) from 2.5 to 40° 2θ was used. A silicon standard was analyzed to check the instrument alignment. Samples were prepared for analysis by placing them in an aluminum/silicon sample holder.

3. Bruker D8 Discover Diffractometer

Samples of polymorph D were analyzed using a Bruker D-8 Discover diffractometer and Bruker's General Area Diffraction Detection System (GADDS, v. 4.1.20). An incident beam of CuKα radiation was produced using a fine-focus tube (40 kV, 40 mA), a Göbel mirror, and a 0.5 mm double-pinhole collimator. The sample was packed between 3-micron thick films to form a portable disc-shaped specimen and analyzed using a transmission geometry. The incident beam was scanned and rastered over the sample during the analysis to optimize orientation statistics. A beam-stop was used to minimize air scatter from the incident beam at low angles. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ. Prior to the analysis a silicon standard was analyzed to verify the Si 111 peak position.

4. Inel XRG-3000 Diffractometer

X-ray powder diffraction (XRPD) analyses of polymorph F were performed using an Inel XRG-3000 diffractometer equipped with a CPS (Curved Position Sensitive) detector with a 2q range of 120°. Real time data were collected using Cu—Kα radiation. The tube voltage and amperage were set to 40 kV and 30 mA, respectively. The monochromator slit was set at 1-5 mm by 160 μm. The patterns are displayed from 2.5-40° 2q. Samples were prepared for analysis by packing them into thin-walled glass capillaries. Each capillary was mounted onto a goniometer head that is motorized to permit spinning of the capillary during data acquisition. The samples were analyzed for 300 seconds. Instrument calibration was performed using a silicon reference standard.

DSC for polymorph A was performed using TA Instruments model Q2000 calorimeter. The samples were placed in an aluminium DSC pan, the weight accurately recorded and the pan crimped. The sample cell was equilibrated at 25° C. and heated under nitrogen purge at a rate of 10° C./min up to a final temperature of 250 or 300° C. Indium metal was used as calibration standard. For all other polymorphs analyses were performed using TA Instruments model 2920 calorimeter. The sample cell was equilibrated at 25° C. and heated under nitrogen purge at a rate of 10° C./min up to a final temperature of 250 or 300° C. Indium metal was used as calibration standard.

TGA analyses were performed on a TA Instruments model 2950 thermogravimetric analyzer. The furnace was equilibrated at 25° C. and heated under nitrogen purge at a rate of 10° C./min up to a final temperature of 300 or 350° C. Nickel and Alume™ were used as calibration standards.

Hotstage microscopy was performed using a Linkam hotstage (model FTIR 600) mounted to a Leica DMLP microscope. Samples were observed using crossed polarized light. Samples were sandwiched between coverslips and visually observed as the stage was heated. The hotstage was calibrated using USP melting point standards.

FT-Raman spectra were acquired on an FT-Raman 960 spectrometer (Thermo Nicolet) using an excitation wavelength of 1064 nm. Approximately 0.2-0.3 W of Nd:YVO$_4$ laser power was used to irradiate the samples. The Raman spectra were measured with a germanium detector. The samples were prepared for analysis by placing the material in a glass tube and positioning the tube in a gold-coated tube holder in the accessory. A total of 256 sample scans were collected from 3600-100 cm$^{-1}$ at a spectral resolution of 4 cm$^{-1}$, using Happ-Genzel apodization. Wavelength calibration was performed using sulfur and cyclohexane.

For $^{13}$C-ss MAS NMR spectroscopy, samples were prepared by packing them into 4 mm PENCIL type zirconia rotors. Acquisition was performed on 1NOVA-400 at ambient temperature using VNMR6.1C (patch a11205) as processing software. The acquisition parameters were as follows:

Sequence: xpolvt1rho1
Relax. Delay: 40.000 sec
Pulse width: 2.2 usec (90.0 deg.) or 2.2 usec (76.2 deg) for polymorph E
Acq. Time: 0.030 sec
Spectral width: 44994.4 Hz (447.517 ppm)
400 scans
2 dummy scans
Acquired points: 2700
Observed Nucleus: C13 (100 MHz)
Decoupled Nucleus: H1 (400 MHz)
SPINAL-64 decoupling
Cross Polarization
Tangent RAMP-CP on C13
Contact time: 5.0 ms
Spinning rate: 12000 Hz

The invention claimed is:

1. A solid pharmaceutical composition comprising a crystal form of 5-[3-(2,5-dichloro-4,6-dimethyl-1-oxy-pyridin-3-yl)[1,2,4]oxadiazol-5-yl]-3-nitrobenzene-1,2-diol having an X-ray powder diffractogram that exhibits peaks at about the following 2θ angles: 5.7, 6.9, 13.8 and 19.6.

2. The pharmaceutical composition according to claim 1, wherein the crystal form of 5-[3-(2,5-dichloro-4,6-dimethyl-1-oxy-pyridin-3-yl)-[1,2,4]oxadiazol-5-yl]-3-nitrobenzene-1,2-diol has an X-ray powder diffractogram exhibiting additional peaks at about the following 2θ angles: 11.9, and 16.9.

3. The pharmaceutical composition according to claim 1, wherein the crystal form of 5-[3-(2,5-dichloro-4,6-dimethyl-1-oxy-pyridin-3-yl)-[1,2,4]oxadiazol-5-yl]-3-nitrobenzene- 1,2-diol has a Raman spectrum exhibiting peaks at about 505, 1292, 1385, 1583, and 1630 cm$^{-1}$.

4. The pharmaceutical composition according to claim 1, wherein the crystal form of 5-[3-(2,5-dichloro-4,6-dimethyl-1-oxy-pyridin-3-yl)-[1,2,4]oxadiazol-5-yl]-3-nitrobenzene-1,2-diol has a Solid State $^{13}$C-NMR spectrum exhibiting peaks at about 150.3, 133.9, 112.6 and 19.8 ppm.

5. The pharmaceutical composition according to claim 1, wherein the crystal form of 5-[3-(2,5-dichloro-4,6-dimethyl-1-oxy-pyridin-3-yl)-[1,2,4]oxadiazol-5-yl]-3-nitrobenzene-1,2-diol has a Differential Scanning calorimetry (DSC) thermogram that exhibits an exotherm at about 237° C.

\* \* \* \* \*